United States Patent [19]

Bass et al.

[11] 4,146,019
[45] Mar. 27, 1979

[54] MULTICHANNEL ENDOSCOPE

[75] Inventors: Michael Bass, Pacific Palisades; Richard M. Dwyer, Glendale, both of Calif.

[73] Assignee: University of Southern California, Los Angeles, Calif.

[21] Appl. No.: 728,228

[22] Filed: Sep. 30, 1976

[51] Int. Cl.² .............................................. A61B 1/06
[52] U.S. Cl. ........................................ 128/6; 128/276
[58] Field of Search ................... 128/4, 6, 7, 8, 348, 128/351, 276, 240, 303.15, 9, 10, 2.05 R, 350 R, DIG. 9

[56] References Cited

U.S. PATENT DOCUMENTS

| 3,368,552 | 2/1968 | Bottcher | 128/4 |
|---|---|---|---|
| 3,426,759 | 2/1969 | Smith | 128/350 R |
| 3,685,509 | 8/1972 | Bentall | 128/2 F |
| 3,726,272 | 4/1973 | Fukami et al. | 128/6 |
| 3,858,577 | 1/1975 | Bass et al. | 128/8 |
| 3,924,608 | 12/1975 | Mitsui | 128/6 |
| 3,941,121 | 3/1976 | Olinger et al. | 128/6 |
| 3,958,566 | 5/1976 | Furihata | 128/4 |
| 3,980,078 | 9/1976 | Tominaga | 128/4 |
| 4,024,858 | 5/1977 | Chikama | 128/4 |

Primary Examiner—Lee S. Cohen
Attorney, Agent, or Firm—Harris, Kern, Wallen & Tinsley

[57] ABSTRACT

A flexible endoscope for insertion into a body cavity for visual observation and medical procedures. A vacuum line slidable in a tube in the endoscope for projection beyond the distal end of the endoscope, with vacuum control, providing for removal of blood clots and the like while observing the operation. A multichannel endoscope providing illumination and viewing, vacuum removal, laser treatment and additional channels for needles, forceps and washing.

6 Claims, 3 Drawing Figures

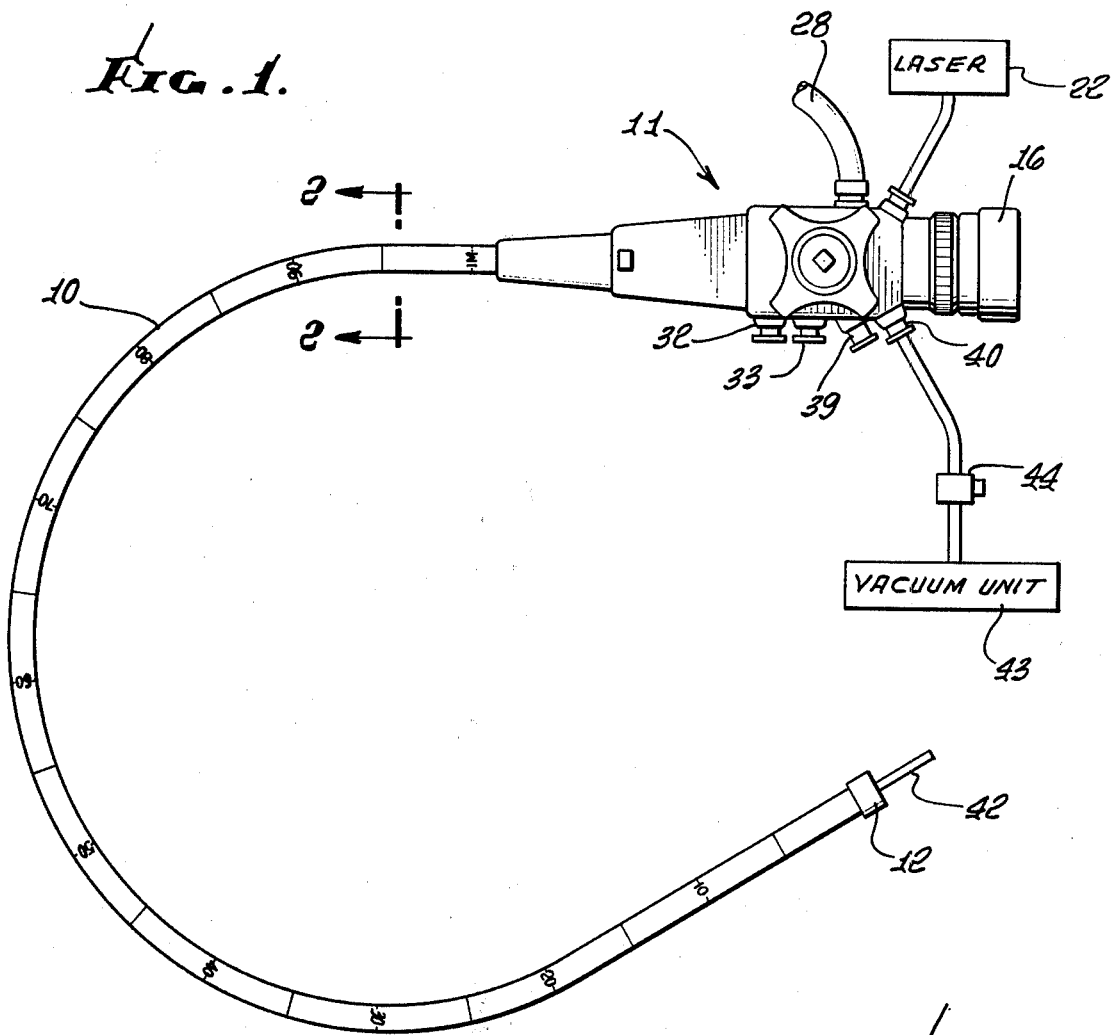
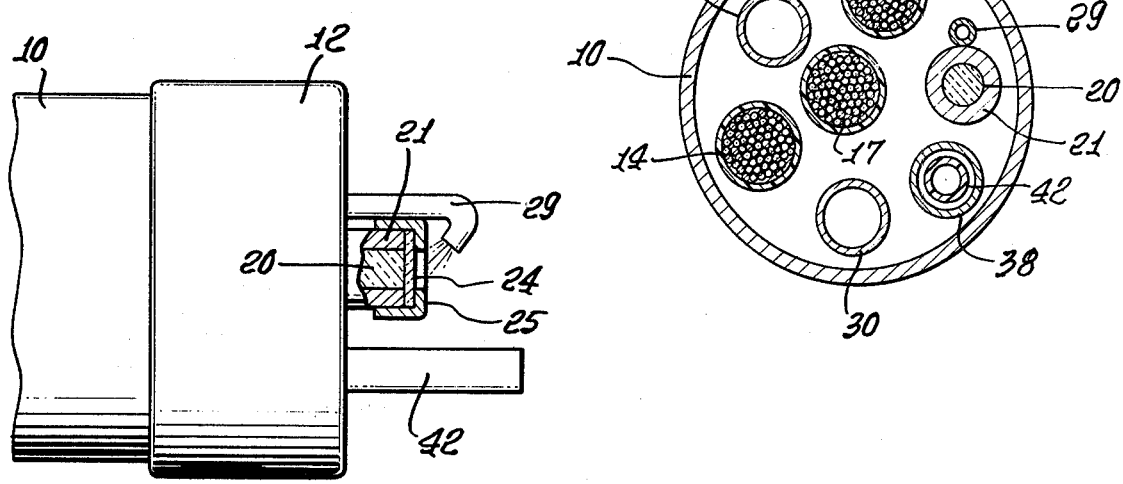

4,146,019

MULTICHANNEL ENDOSCOPE

BACKGROUND OF THE INVENTION

This invention relates to endoscopes and in particular, to a new and improved multichannel endoscope which permits various medical procedures while observing the body cavity.

Multichannel endoscopes are in wide use for examination of the inner surface of a body cavity, such as the stomach wall. The endoscope has a flexible tube which is inserted into the body cavity and typically carries one or two bundles of fiber-optic fibers providing illumination and another bundle of fiber-optic fibers for viewing. Additional tubes are incorporated in the main tube providing passages for air or water for flushing, suction and medical tools such as forceps and needles. Instruments of this type include the Olympus Gastrointestinal Fiberscope Model GIF Type D3, the American Cystoscope Panendoscope Model F8, and the Machida Fiber Colonoscope Model FCS-S. Endoscopes are now being built incorporating a laser beam channel for delivering laser energy to the internal surface of the body cavity, and a typical instrument is shown in U.S. Pat. No. 3,858,577.

However some problems have been encountered with the presently available instruments. The conventional instruments do provide for connecting a vacuum source to a tube within the endoscope to provide a suction at the distal end. However it has been difficult to control the suction, the tubes are subject to clogging, and the suction is not easily directed within the body cavity. Also, the conventional endoscopes have a limited number of channels and doctors cannot perform all the procedures desired in a single unit.

Accordingly, it is an object of the present invention to provide a new and improved endoscope incorporating a separate suction line within a tube of the endoscope, which line can be inserted and removed as desired and which can be projected beyond the distal end of the instrument for removing individual blood clots and the like while observing the procedure through the view optics. A further object is to provide an improved control for the suction line. An additional object of the invention is to provide a new and improved endoscope incorporating additional channels providing for carrying out a number of procedures through the single instrument.

SUMMARY OF THE INVENTION

A flexible endoscope with an illumination channel and a viewing channel and a passage for slidingly receiving a suction line, which line can be inserted and withdrawn while the endoscope is in position in the patient, with the distal end of the suction line being positionable beyond the distal end of the endoscope permitting illumination and viewing of a work surface while the suction line is being used for removing blood clots and the like. A flexible endoscope with illumination and viewing channels, a tube for a suction line, a laser beam delivery channel, and additional tubes for medical tools, washing fluid, and laser distal end cleaning fluid. A control for the suction system providing the operator with close control over suction during medical procedures.

BRIEF DESCRIPTION OF THE DRAWING

FIG. 1 is an illustration of an endoscope incorporating the presently preferred embodiment of the invention;

FIG. 2 is an enlarged sectional view taken along the line 2—2 of FIG. 1; and

FIG. 3 is an enlarged view of the distal end of the endoscope of FIG. 1.

DESCRIPTION OF THE PREFERRED EMBODIMENT

The endoscope of FIG. 1 includes a flexible tube 10 with a control housing 11 at the proximal end. A light source is mounted in the housing and provides illumination to the distal end 12 through bundles 13, 14 of fiber-optic fibers positioned within the tube 10. A viewing system is also mounted in the housing, with eyepiece 16 for viewing through the distal end via another bundle 17 of fiberoptic fibers. The illumination and viewing channels with light source and optics may be conventional in design.

Means are also provided in the tube 10 for delivering laser energy at the distal end and the system shown in U.S. Pat. No. 3,858,577 may be used. A single glass fiber 20 in a protective sheath 21 may be positioned within the tube 10, with a laser 22 positioned at the distal end of the fiber 20 for directing laser radiation into the fiber 20. A transparent window 24 may be positioned at the distal end of the fiber 20 and held in place by a cap 25.

A source of water or other fluid may be connected to the housing 11 via a line 28. Lines 29 and 30 may be positioned in the tube 10, with the distal end of the line 20 positioned for directing fluid onto the window 24. The distal end of the line 30 may be positioned for directing a washing fluid onto the distal end of the bundles 13, 14, 17 or onto the work surface as desired. In the housing, a valve 32 controls flow of fluid from the line 28 to the line 29 and another valve 33 controls flow of fluid from the line 28 to the line 30.

Tubes 37, 38 are also positioned within the tube 10, with the distal end of the tube 37 on the housing at 39 and with the distal end of the tube 38 on the housing at 40. A medical tool such as forceps or a needle for delivering medication may be inserted through the tube 37.

A suction line 42, typically a piece of plastic tubing such as ⅛ inch outside diameter polypropylene tubing is positioned in the tube 38. The suction line 42 slides within the tube 38 so that the suction line can be inserted and removed as desired while the endoscope is in position in the patient. A vacuum unit 43 is connected at the distal end of the suction line 42 with a control valve 44 in the line. Preferably, the control valve normally opens the line 42 to the atmosphere so that there is no vacuum in the line until the valve is actuated. In its simplest form, the valve may be an opening which the operator closes with a thumb or finger, with the throttling of the opening providing the operator a fine control on the magnitude of suction.

In use, the distal end of the suction line 42 may be projected outward from the distal end of the tube 10 permitting the operator to view the end of the suction line and easily use the suction line for removing blood clots and other items from the cavity. Suction systems have been used in endoscopes and have encountered problems with collapse and with clogging. The suction line 42 positioned within the tube 38 works very satisfactorily with pressure differentials in the order of 15 pounds per square inch. If for any reason the line clogs, the line is easily removed from the endoscope, cleaned and reinserted for continuing the medical procedure.

The endoscope of the invention with the plurality of tubes permits the operator to perform a plurality of procedures at the same time or in sequence while using the single instrument. The possibilities include illumination and viewing, laser coagulation and cauterization, washing and flushing, suction removal, tissue sample taking with forceps, and medication injection with needles.

We claim:

1. In an instrument for simultaneously viewing an internal surface of a body cavity such as a stomach and performing a medical procedure on the internal surface from an external position, the combination of:

a flexible endoscope comprising a tube in the order of one half inch diameter and several feet in length, and having a distal end and a proximal end and having a first illumination channel, a second viewing channel, and a third channel, each channel being within said tube and providing a passage between said ends; and a suction line having first and second ends and positioned within said third channel, with said first end projecting from said proximal end for connection to a vacuum source, with said suction line slidable in said third channel and of sufficient length for projecting said second end of said line beyond the distal end of said tube with the first end still projecting from the proximal end, for positioning said second end at said internal surface with said tube distal end spaced from said internal surface and for removing and replacing said line in said third channel without disturbing said endoscope.

2. An instrument as defined in claim 1 including a valve positioned in said line adjacent said tube proximal end for control of suction in said line, with said valve normally providing an opening in said line to the atmosphere.

3. An instrument as defined in claim 2 including a fourth laser beam channel in said tube and having a distal end adjacent the tube distal end and means for coupling the output of a laser to said fourth channel at said tube proximal end for delivering laser energy to said tube distal end.

4. An instrument as defined in claim 3 including a transparent window carried at the distal end of said fourth channel, and a fifth channel in said tube, said fifth channel having an outlet adjacent said window for delivering a fluid stream at the exposed surface of said window.

5. An instrument as defined in claim 4 including a sixth channel in said tube providing a passage between said tube ends for slidingly receiving a medical tool.

6. An instrument as defined in claim 5 including a seventh channel in said tube providing a passage between said tube ends for delivering a fluid stream to the body cavity.

* * * * *